(12) United States Patent
Rutti et al.

(10) Patent No.: US 7,815,607 B2
(45) Date of Patent: *Oct. 19, 2010

(54) INSERTION DEVICE FOR AN INSERTION HEAD, IN PARTICULAR FOR AN INFUSION SET

(75) Inventors: Pascal Rutti, Neuendorf (CH); Jurg Liniger, Ostermundigen (CH); Allen Pearson, Cambridgeshire (GB); Tom Kelsey, Cambridge (GB)

(73) Assignee: Roche Diagnostics International AG, Steinhausen (CH)

( * ) Notice: Subject to any disclaimer, the term of this patent is extended or adjusted under 35 U.S.C. 154(b) by 116 days.

This patent is subject to a terminal disclaimer.

(21) Appl. No.: 12/047,643

(22) Filed: Mar. 13, 2008

(65) Prior Publication Data

US 2008/0249473 A1 Oct. 9, 2008

(30) Foreign Application Priority Data

Mar. 14, 2007 (EP) .................................. 07005216

(51) Int. Cl.
*A61M 5/20* (2006.01)
(52) U.S. Cl. ..................................................... 604/157
(58) Field of Classification Search .............. 604/890.1, 604/164.12, 157, 164.08
See application file for complete search history.

(56) References Cited

U.S. PATENT DOCUMENTS

| | | |
|---|---|---|
| 4,306,563 A | 12/1981 | Iwatschenko |
| 4,631,058 A | 12/1986 | Raines |
| 4,755,173 A | 7/1988 | Konopka et al. |
| 4,835,248 A | 5/1989 | Bader et al. |
| 4,863,432 A | 9/1989 | Kvalo |
| 4,927,603 A | 5/1990 | Fischer et al. |
| 4,968,303 A | 11/1990 | Clarke et al. |
| 5,176,662 A | 1/1993 | Bartholomew et al. |
| 5,522,803 A | 6/1996 | Teissen-Simony |
| 5,545,143 A | 8/1996 | Fischell |
| 5,584,813 A | 12/1996 | Livingston et al. |

(Continued)

FOREIGN PATENT DOCUMENTS

DE 19821723 A1 11/1999

(Continued)

OTHER PUBLICATIONS

European Search Report for 07005215.

(Continued)

*Primary Examiner*—Nicholas D Lucchesi
*Assistant Examiner*—Brooke M Matney
(74) *Attorney, Agent, or Firm*—Dinsmore & Shohl LLP

(57) ABSTRACT

An insertion device for an infusion set, the device including a retention means by which the infusion set can be temporarily held on the device and drive means including a pretensionable spring for providing drive energy for an insertion movement of the infusion set, wherein the infusion set is secured by the retention means by clamping when the retention means is in an engage position and can then be moved, with simultaneous pretensioning of the spring, to an insertion movement starting position, wherein the infusion set is already separated from the retention means at the start of the insertion movement, and wherein the infusion set moves through at least part of the insertion movement free of the retention means.

34 Claims, 10 Drawing Sheets

U.S. PATENT DOCUMENTS

| | | | |
|---|---|---|---|
| 5,637,094 A * | 6/1997 | Stewart et al. | 604/135 |
| 5,814,020 A | 9/1998 | Gross | |
| 5,848,990 A * | 12/1998 | Cirelli et al. | 604/136 |
| 5,858,001 A | 1/1999 | Tsals et al. | |
| 5,951,522 A | 9/1999 | Rosato et al. | |
| 5,957,895 A | 9/1999 | Sage et al. | |
| 5,968,011 A | 10/1999 | Larsen et al. | |
| 5,980,506 A | 11/1999 | Mathiasen | |
| 5,997,504 A | 12/1999 | Bell | |
| 6,017,328 A | 1/2000 | Fischell et al. | |
| 6,056,718 A | 5/2000 | Funderburk et al. | |
| 6,090,068 A | 7/2000 | Chanut | |
| 6,261,259 B1 | 7/2001 | Bell | |
| 6,302,866 B1 | 10/2001 | Marggi | |
| 6,355,021 B1 | 3/2002 | Nielsen et al. | |
| 6,379,335 B1 | 4/2002 | Rigon et al. | |
| 6,419,699 B1 | 7/2002 | Schuessler | |
| 6,500,150 B1 | 12/2002 | Gross et al. | |
| 6,520,938 B1 | 2/2003 | Funderburk et al. | |
| 6,537,255 B1 | 3/2003 | Raines | |
| 6,579,267 B2 | 6/2003 | Lynch et al. | |
| 6,607,509 B2 | 8/2003 | Bobroff et al. | |
| 6,676,633 B2 | 1/2004 | Smith et al. | |
| 6,749,588 B1 | 6/2004 | Howell et al. | |
| 6,749,589 B1 | 6/2004 | Douglas et al. | |
| 6,755,805 B1 | 6/2004 | Reid | |
| 6,824,530 B2 | 11/2004 | Wagner et al. | |
| 6,840,922 B2 | 1/2005 | Nielsen et al. | |
| 6,878,134 B2 | 4/2005 | Rogers et al. | |
| 6,887,270 B2 | 5/2005 | Miller et al. | |
| 6,911,020 B2 | 6/2005 | Raines | |
| 6,921,388 B2 | 7/2005 | Swenson | |
| 6,923,791 B2 | 8/2005 | Douglas | |
| 6,949,084 B2 | 9/2005 | Marggi et al. | |
| 6,969,372 B1 | 11/2005 | Halseth | |
| 6,997,902 B2 | 2/2006 | Thorne et al. | |
| D526,409 S | 8/2006 | Nielsen et al. | |
| 7,097,637 B2 | 8/2006 | Triplett et al. | |
| 7,147,623 B2 | 12/2006 | Mathiasen | |
| 7,214,207 B2 | 5/2007 | Lynch et al. | |
| 2002/0045867 A1 | 4/2002 | Nielsen et al. | |
| 2002/0123724 A1 | 9/2002 | Douglas et al. | |
| 2002/0193744 A1 | 12/2002 | Alesi et al. | |
| 2003/0069546 A1 | 4/2003 | Sandstrom et al. | |
| 2003/0083624 A1 | 5/2003 | Smith et al. | |
| 2003/0105449 A1 | 6/2003 | Raines | |
| 2003/0125669 A1 | 7/2003 | Safabash et al. | |
| 2003/0181874 A1 | 9/2003 | Bressler et al. | |
| 2003/0199823 A1 | 10/2003 | Bobroff et al. | |
| 2004/0044306 A1 | 3/2004 | Lynch et al. | |
| 2004/0158207 A1 | 8/2004 | Hunn et al. | |
| 2004/0158230 A1 | 8/2004 | Hunn et al. | |
| 2004/0215154 A1 | 10/2004 | Hwang et al. | |
| 2005/0035014 A1 | 2/2005 | Crane | |
| 2005/0283125 A1 | 12/2005 | Barkhahn et al. | |
| 2006/0015063 A1 | 1/2006 | Butikofer et al. | |
| 2006/0030824 A1 | 2/2006 | Hunn et al. | |
| 2006/0173414 A1 | 8/2006 | Buetikofer et al. | |
| 2006/0183985 A1 | 8/2006 | Brister et al. | |
| 2006/0229573 A1 | 10/2006 | Lamborne | |
| 2007/0016149 A1 | 1/2007 | Hunn et al. | |
| 2007/0129688 A1 | 6/2007 | Scheurer et al. | |

FOREIGN PATENT DOCUMENTS

| | | | |
|---|---|---|---|
| DE | 10117286 A1 | | 10/2002 |
| DE | 20320207 U1 | | 11/2004 |
| DE | 202004017862 | * | 3/2005 |
| DE | 102004002472 A1 | | 8/2005 |
| DE | 102004039408 A1 | | 3/2006 |
| EP | 1652547 A1 | | 5/2006 |
| EP | 1764125 A1 | | 3/2007 |
| FR | 2725902 A1 | | 4/1996 |
| FR | 2752164 A1 | | 2/1998 |
| WO | 02081012 A2 | | 10/2002 |
| WO | 2004029457 A1 | | 4/2004 |
| WO | 2004064593 A2 | | 8/2004 |
| WO | 2004064898 A1 | | 8/2004 |
| WO | 2004098682 A2 | | 11/2004 |
| WO | 2004101071 A2 | | 11/2004 |
| WO | 2004110527 A1 | | 12/2004 |
| WO | 2005037184 A1 | | 4/2005 |
| WO | 2005065748 A1 | | 7/2005 |
| WO | 2006015507 A1 | | 2/2006 |
| WO | 2006108185 A1 | | 10/2006 |
| WO | 2006129196 A1 | | 12/2006 |

OTHER PUBLICATIONS

European Search Report for 07005216.
European Search Report for 07005217.
US Office Action dated Jan. 11, 2010 pertaining to U.S. Appl. No. 12/047,666.
US Notice of Allowance dated Jun. 7, 2010 pertaining to U.S. Appl. No. 11/673,939.
US Office Action dated Mar. 24, 2010 pertaining to U.S. Appl. No. 11/673,939.
US Office Action dated Dec. 29, 2009 pertaining to U.S. Appl. No. 11/673,939.
US Office Action dated May 27, 2009 pertaining to U.S. Appl. No. 11/673,939.
US Office Action dated Jul. 11, 2008 pertaining to U.S. Appl. No. 11/673,939.
US Office Action dated Nov. 28, 2007 pertaining to U.S. Appl. No. 11/673,939.
US Office Action dated Jun. 14, 2007 pertaining to U.S. Appl. No. 11/673,939.
US Notice of Allowance dated Apr. 2, 2010 pertaining to U.S. Appl. No. 12/047,551.
US Office Action dated Dec. 23, 2009 pertaining to U.S. Appl. No. 12/047,551.
US Office Action dated Sep. 17, 2009 pertaining to U.S. Appl. No. 12/047,551.

* cited by examiner

INSERTION DEVICE FOR AN INSERTION HEAD, IN PARTICULAR FOR AN INFUSION SET

CROSS REFERENCE TO RELATED APPLICATIONS

This application claims priority to European Application No. 07005216.2, filed on Mar. 14, 2007, the contents of which are hereby incorporated in their entirety by reference herein.

BACKGROUND

The present invention relates to devices for injecting, infusing, delivering, administering or dispensing substances, and to methods of making and using such devices. More particularly, it relates to an insertion device for an insertion head, an arrangement comprising the insertion device and an insertion head that is or can be received in the device, a use of the insertion device or of the arrangement, and a method for applying or using an insertion head.

In patients with a regular requirement for a medicament that can be administered by direct delivery into the body tissue or into the blood stream, for example certain groups of patients suffering from pain, or patients with type I and type II diabetes, it can be useful to supply the body with the required quantity of medicament in liquid form via a cannula that is introduced at a suitable location into the body and that remains there over quite a long period of time. For this purpose, a cannula arrangement, designated as an infusion set or port, depending on its design, is secured on the patient's skin, such that the cannula passes through the skin and into the body.

Efforts are also increasingly being made to monitor certain medical parameters of a patient, for example the blood sugar value, continuously over quite a long period of time. For this purpose, a sensor arrangement, for example, is placed on the patient's body and, with a puncturing tip of a suitable sensor, passes through the skin and into the patient's body.

To avoid infections, the infusion set, the port or the sensor arrangement has to be changed at regular intervals, for example every three days. In outpatient treatment, for example in the case of diabetics, this is often done by the patients themselves and, on account of the introduction of the infusion cannula or of the puncturing tip into the skin, is associated with a certain amount of pain. It is therefore important that such infusion sets, ports or sensor arrangements can be applied easily and safely, which is why many manufacturers have started designing their products as insertion heads for special insertion devices with the aid of which the insertion heads can be applied to the patient's body. Application is made easier in this way, and the pain occasioned by the application is reduced to a minimum, thanks to the quick and targeted puncturing procedure.

Thus, for example, U.S. Pat. No. 6,607,509 B2 discloses insertion devices for infusion sets, in which the infusion set is placed abruptly onto the application site by the force of a pretensioned spring, and the cannula penetrates into the tissue of the patient. After application of the infusion set, the insertion device has to be uncoupled and removed from the infusion set, which has the disadvantage that this may cause irritation at the puncture site by force exerted on the inserted cannula.

WO 2004/110527 A1 discloses, in addition to insertion devices as described above, also a similar insertion device for infusion sets in which, however, the infusion set is already automatically separated from the insertion device at the start of the insertion movement and then penetrates in free flight into the body of the patient. Compared to the previously described insertion devices, this arrangement affords the advantage that, during the actual puncturing movement, practically no friction losses occur within the insertion device, such that the application can take place at great speed and with a correspondingly short pain interval. Irritation at the puncture site, caused by subsequent detachment of the insertion device from the insertion head, is also avoided. However, said insertion device has the disadvantage of being relatively complicated to use and of requiring a large number of operating steps.

SUMMARY

An object of the present invention is therefore to make available an insertion device, an arrangement comprising an insertion device with an associated insertion head, and a method for applying or using an insertion head, all of which do not have, or at least partially avoid, the disadvantages of the prior art.

In one embodiment, the present invention comprises an insertion device for an infusion set, the device comprising a retainer by which the infusion set can be temporarily held on the device and driver comprising a pretensionable spring for providing drive energy for an insertion movement of the infusion set, wherein the infusion set is secured by the retainer by clamping when the retainer is in an engage position and can then be moved, with simultaneous pretensioning of the spring, to an insertion movement starting position, wherein the infusion set is already separated from the retainer at the start of the insertion movement, and wherein the infusion set moves through at least part of the insertion movement free of the retainer.

In one embodiment, the present invention comprises an insertion device for an infusion set, the device comprising a retention means by which the infusion set can be temporarily held on the device and drive means comprising a pretensionable spring for providing drive energy for an insertion movement of the infusion set, wherein the infusion set is secured by the retention means by clamping when the retention means is in an engage position and can then be moved, with simultaneous pretensioning of the spring, to an insertion movement starting position, wherein the infusion set is already separated from the retention means at the start of the insertion movement, and wherein the infusion set moves through at least the greatest part of the insertion movement free of the retention means.

Accordingly, a first aspect of the present invention concerns an insertion device for an insertion head with at least one infusion cannula and/or at least one puncturing tip. An insertion head to be applied with the insertion device can therefore comprise, for example, a single infusion cannula or a single puncturing tip, several cannulas or several puncturing tips, or one or more cannulas and one or more puncturing tips and, furthermore, can be designed, for example, as an infusion set, as a port and/or as a sensor arrangement, for example for measuring the blood sugar value. The insertion device has one or more contact faces, which are formed by a housing and with which the insertion device is placed onto the skin of the patient for application of the insertion head. The insertion device also comprises a retainer or retention means, for example two mutually opposite leaf spring elements, with which the insertion head to be applied can be temporarily held on, by or to the insertion device, with the result that, during the actual application of the insertion head, only the insertion device has to be held by the user on the application site.

In some embodiment, the insertion device further comprises a driver or drive means, which comprises at least one pretensionable energy-storing element, for example a helical spring, for providing the drive energy, and with which the insertion head to be applied can be moved, relative to the contact face in the longitudinal direction of an infusion cannula or puncturing tip, from a first position, in which it is held by the retention means such that all its infusion cannulas and puncturing tips are set back relative to the contact face, for avoiding inadvertent contact with the user, to a second position, in which all its infusion cannulas and puncturing tips protrude substantially completely beyond the contact face, to permit introduction of these infusion cannulas and puncturing tips into the body of the patient when the insertion device is placed with the contact face on the skin of the patient. This movement of the insertion head, which is driven by the energy-storing element and takes place with increasing relaxation of the latter, and by which the insertion head is actually applied to the body, is designated and/or may be thought of as the insertion movement. The retention means of the insertion device can be positioned relative to the contact face in an engage position and in a standby position and are designed such that the insertion head to be applied can be arranged on the retention means in the engage position such that it is held on these, and the retention means, starting from the engage position with the insertion head held on them, can then be brought to the standby position. On reaching the standby position, the retention means hold the insertion head in the first position ready for application, i.e. in the state ready for introduction into the skin. Moreover, the insertion device is designed such that the insertion head is separated from the retention means at the start of the insertion movement, such that it can execute the greatest part of the insertion movement free of the retention means, e.g. in "free flight" or, at any rate, guided by lateral guides, and, after application, there is no longer any connection between the insertion head and the insertion device, with the result that the insertion device can be removed from the insertion head applied to the body, without any danger of irritation of the application site. The insertion device is also designed such that the pretensionable energy-storing element is automatically pretensioned during the movement of the retention means, with the insertion head held thereon, from the engage position to the standby position.

The present invention permits the provision of insertion devices for insertion heads which have a very short insertion phase with a correspondingly short pain interval, avoid irritation of the puncture site upon release of the insertion head from the insertion device, and at the same time are much easier to use than the insertion devices of this type known today.

In a preferred embodiment, the insertion device is designed such that the insertion head can be held in the first position by the retention means purely with a force fit, purely with a form fit, or with a combination of a force fit and form fit. In particular, in the case of a purely force fit, the advantage is that the insertion head, at the start of the insertion movement, can be easily knocked out of the retention means by a thrust element of the drive means and is thus released from said retention means.

It is further preferred for the insertion device to be designed such that the insertion head can be held in the engage position by the retention means purely with a form fit or with a combination of a force fit and form fit, and it may be preferable for the insertion device to be designed such that the form fit is cancelled during the movement of the retention means, with the insertion head held therein, from the engage position to the standby position.

Alternatively, in some preferred embodiments, the insertion head can be held in the engage position by the retention means purely with a force fit, and the force fit is reduced during the movement of the retention means, with the insertion head held therein, from the engage position to the standby position. This can be achieved, for example, by the insertion head being held with a force fit by spring shackles whose free resilient length increases during the movement of the retention means from the engage position to the standby position. However, alternative embodiments are also possible in which there is purely a force fit of equal strength both in the engage position and also in the standby position.

In the alternative embodiments in which a form fit is cancelled or a force fit is reduced during the movement of the retention means, with the insertion head held therein, from the engage position to the standby position, an advantage, especially when using insertion heads with a fixed infusion cannula or puncturing tip, is that the insertion head is held more firmly in the engage position than in the standby position, with the result that the needle guard or cannula guard can be removed without any danger of the insertion head coming loose again from the retention means.

In another preferred embodiment, the insertion device is designed such that, at least during a large part of the insertion movement or during the entire insertion movement of the insertion head, the retention means remain unmoved relative to the contact face or contact faces. In this way, insertion devices according to the present invention can be made available that are of simple construction.

In another preferred embodiment, the insertion device has manually activatable actuation means, for example a slide element, a rotary knob or a push button, by which the retention means, with the insertion head held thereon, can be brought manually by muscle force from the engage position to the standby position, that is to say by maneuvering the retention means with one hand or both hands, at the same time with pretensioning of the energy-storing element.

In some preferred embodiments, the insertion device comprises a housing, and the retention means are connected rigidly to an actuation means in the form of a slide element, which can be gripped by hand and can be moved, e.g. displaced, relative to the housing, to move the retention means from the engage position to the standby position, at the same time with pretensioning of the energy-storing element. This permits the provision of inexpensive and purely mechanical insertion devices, which are ready to be used at any time without external energy. This is in contrast to other preferred embodiments of the insertion device according to the present invention in which the pretensioning is obtained by electrical elements, for example by an electric motor. In such embodiments, the actuation means can comprise switches and/or sensors that control the electrical elements for pretensioning the energy-storing elements.

In yet another preferred embodiment, the insertion device is designed such that its overall dimensions remain unchanged during the movement of the retention means from the engage position to the standby position. Such devices have the advantage that they can be made compact and robust and, in the storage state, in which the energy-storing elements ought to be relaxed and not pretensioned ready for application, their dimensions are no greater than in the pretensioned state ready for application, which makes it easier to store and transport the application device, for example in a handbag.

It is also advantageous for the insertion device to be designed such that the energy-storing element can be pretensioned repeatedly by the user, to allow the insertion device to be used several times for application of an insertion head.

In some preferred embodiments, with the insertion head located in the first position, the energy-storing element can be made ready in the pretensioned state, and the insertion movement can then be triggered by actuation of one actuation member, or by simultaneous or sequential actuation of several actuation members, with relaxation of the energy-storing element. Suitable actuation members can be of a purely mechanical construction, for example as trigger latches or trigger slides, or can, for example, also comprise electrical or electronic elements, for example an electrically activated latch that can be triggered via a switch and/or a sensor with evaluation electronics. This favors a controlled application of the insertion head.

It is also advantageous if the drive means comprises a thrust element for transmitting the drive energy to the insertion head to be applied and is designed such that, by displacing the thrust element counter to the direction of the insertion movement and subsequently locking it with a lock or locking means that can be released by the actuation members, the energy-storing element can be pretensioned and made ready in the pretensioned state. Such constructions can be produced inexpensively, function in a reliable manner and also permit a high initial acceleration and, consequently, a rapid insertion movement, thereby minimizing the pain that is occasioned by the application upon introduction of the infusion cannula or of the puncturing tip into the body.

In insertion devices according to the present invention in which the energy-storing element can be made ready in the pretensioned state when the insertion head is located in the first position, and the insertion movement can then be triggered by actuation of an actuation member, it may be preferred that the insertion device has at least two actuation members, which have to be actuated simultaneously to trigger the insertion movement. A first of the actuation members can be actuated by the contact face of the insertion device being pressed onto the body of the patient, e.g. by its being pressed on in the direction of the insertion movement, which is especially advantageous if the insertion is performed at an angle of approximately 90° to the surface of the body. This embodiment of the insertion device considerably reduces the danger of inadvertent triggering of the insertion device when ready for application, and thus also considerably reduces the chances of the user sustaining an injury.

In some embodiments, the first actuation member is a slide-shaped or button-shaped element, and this at the same time forms the entire contact face or, if there are several contact faces, it forms all the contact faces of the insertion device. The advantage of this is that the first actuation member can be safely actuated independently of the surface contour of the application site on the patient's body.

As an alternative to purely mechanical embodiments of the first actuation member, electrical first actuation members may be used. This is possible, for example, in the form of an electrical latch element which is controlled by one or more skin contact sensors (e.g. conductivity sensors) arranged on the contact face and by associated control electronics, such that it is activated when the insertion device is placed correctly onto the application site.

In preferred embodiments of the insertion device with at least two actuation members, at least one of the actuation members, e.g. the second actuation member, is a button-shaped element which can be actuated when a user presses it with a finger tip. The actuation direction is transverse or perpendicular to the direction in which the insertion device is pressed onto the body of the patient, which direction is the same as the direction of the insertion movement and, consequently, the direction of introduction of the infusion cannula or puncturing tip into the skin. This second actuation member can be of a purely mechanical construction, for example as trigger latch or trigger slide, or can, for example, also comprise electrical or electronic elements, for example an electrically activated latch that can be triggered via a switch and/or a sensor with evaluation electronics. By this embodiment, it is possible to further reduce the danger of inadvertent actuation of this actuation member together with the first actuation member, thereby lessening the danger of inadvertent triggering.

In some embodiments, it may be advantageous if the direction of actuation is parallel or substantially parallel to the direction of pressing-on.

In yet another preferred embodiment of the insertion device according to the present invention with at least two actuation members, its actuation members, which are to be actuated to trigger the insertion movement, are coupled to one another such that, by actuating one of the actuation members, a blocking of another actuation member or of several other of actuation members can be cancelled. In this way, the construction can be simplified, since only a single trigger mechanism is necessary. If one actuation member with electrical elements is present, a simple and inexpensive structure can be produced, for example by an electrical latch element that can only be triggered when two switches or sensors are actuated simultaneously or a combination of at least one switch and at least one sensor.

In yet another preferred embodiment of the insertion device with one or at least two actuation members, all the actuation members, which have to be actuated simultaneously to trigger or initiate the insertion movement, are designed such that they can be actuated with one hand by the user. Accordingly, one-handed operation of the insertion device is possible, as a result of which the insertion head can be applied by the patient even in areas of the body that are inaccessible with both hands or are difficult to access with both hands, for example in the area of the hips.

In a preferred embodiment of the insertion device with one or more actuation members, the actuation members, which have to be actuated simultaneously to trigger the insertion movement, are designed such that, when an actuating force ceases, they automatically readopt or return to their unactuated state. This further increases the degree of safety against inadvertent triggering of the insertion device.

If the drive means of the insertion device comprises one or more energy-storing elements for providing the drive energy for the insertion movement, for example helical springs, leg springs or leaf springs made of metal or plastic, pneumatic compression springs or rubber spring elements, which is the case, the insertion device can be used at any time and in any place, independently of external sources of energy, and can also be made inexpensively.

In another preferred embodiment, the insertion device has means for effecting a displacement, e.g. a transverse displacement, of a displaceable actuation member of an insertion head to be held in the retention means, with one or several deployable infusion cannulas and/or one or several deployable puncturing tips, during the movement of the retention means, with the insertion head held correctly therein, from the engage position to the standby position, so as to permit automatic deployment of all the deployable infusion cannulas and all the deployable puncturing tips of the insertion head during the movement from the engage position to the standby position.

In this way, it is possible for insertion heads adapted to the insertion device and with deployable infusion cannulas or puncturing tips to be fitted in the protected state, i.e. with the cannulas or puncturing tips folded inwardly, into the retention means of the insertion device that are positioned in the engage position, and for the insertion head to be then automatically made ready for application by moving it together with the retention means into the first position, with simultaneous pretensioning of the energy-storing element and deployment of the cannulas and puncturing tips. In this way, the danger of the user being injured by the cannulas or the puncturing tips, when preparing for the application of the insertion head, can be practically eliminated.

In the embodiment described above, the means for effecting a displacement of a displaceable actuation member may comprise a ramp surface or are designed as a ramp surface on which a transversely displaceable actuation member of a correspondingly designed insertion head can run or move during the movement of the retention means, with the insertion head held correctly therein, from the engage position to the standby position, and in so doing can be displaced transverse to the direction of movement of the retention means and of the insertion head, to permit deployment of the deployable infusion cannulas and puncturing tips of the insertion head. Such means for effecting displacement of a displaceable actuation member can be readily made available in a simple and inexpensive way.

In the two embodiments described above, it may be preferable if the means for effecting a displacement of a displaceable actuation member comprise a lever mechanism with which a displaceable, e.g. a transversely displaceable actuation member of a correspondingly designed insertion head, can be displaced transverse to the direction of movement of the retention means and of the insertion head during the movement of the retention means, with the insertion head held correctly therein, from the engage position to the standby position, to permit deployment of the deployable infusion cannulas and puncturing tips of the insertion head. This permits considerable freedom in terms of the structural configuration both of the insertion device and also of the associated insertion head.

A second aspect of the present invention concerns an arrangement that comprises an insertion device according to the first aspect of the present invention, and an insertion head which is or can be received in the latter and which is designed as an infusion set, port and/or sensor arrangement and has at least one infusion cannula and/or at least one puncturing tip. The insertion head can therefore have, for example, a single infusion cannula or puncturing tip, several cannulas or puncturing tips, or one or more cannulas and one or more puncturing tips. By engaging a suitable matching insertion head into the inventive insertion device according to the first aspect of the present invention, such an inventive arrangement is necessarily achieved. In addition to the marketing of inventive reusable insertion devices according to the first aspect of the present invention and of associated insertion heads, such as associated infusion sets, ports or sensor arrangements, which are joined together by the user shortly before use to form arrangements according to the present invention, provision is also made for preassembled arrangements according to the present invention to be offered as disposable articles, with the insertion device being disposed of after the insertion head has been applied.

In a preferred embodiment of the arrangement according to the present invention, the insertion head is an insertion head with at least one deployable infusion cannula and/or at least one deployable puncturing tip, all the deployable infusion cannulas and puncturing tips of the insertion head being folded inwardly in the unactuated state, in which the insertion head is intended to be engaged in the retention means arranged in the engage position or is already held in the retention means arranged in the engage position, and the insertion device and the insertion head being designed such that all the deployable infusion cannulas and puncturing tips of the insertion head are deployed during the movement of the retention means, with the insertion head held correctly therein, from the engage position to the standby position. As has already been mentioned in the discussion of other aspects of the present invention, this can practically rule out any danger of the user being injured by the cannula or puncturing tip when preparing to apply the insertion head.

A third aspect of the present invention concerns the use of the insertion device or of the arrangement according to the present invention for applying an insertion head to the body of a patient, e.g. an insertion head designed as an infusion set, port or sensor arrangement and having at least one infusion cannula and/or at least one puncturing tip. Such uses are in accordance with the present invention and bring out clearly the advantages of the present invention.

A fourth aspect of the present invention concerns a method for applying an insertion head to the body of a patient, e.g. an insertion head designed as an infusion set, port or sensor arrangement, using an insertion device according to the first aspect of the present invention.

In a first method step, the insertion device is made ready with the retention means arranged in the engage position. Then, an insertion head adapted to the insertion device, and with at least one infusion cannula and/or at least one puncturing tip, is engaged into or by the retention means, such that it is held by the retention means. An inventive arrangement according to the second aspect of the present invention is thus present in which the insertion head can have a single infusion cannula or puncturing tip, several cannulas or puncturing tips, or one or more cannulas and one or more puncturing tips.

Then, in a third step, the retention means are moved from the engage position, with the insertion head held correctly thereon, and with pretensioning of the pretensionable energy-storing element of the insertion device, to the standby position in which the insertion head, after reaching the standby position, is held ready for application by the retention means in the first position. The insertion device is now ready for the actual application process.

For this purpose, the insertion device, in another step of the method according to the present invention, is arranged with the contact face of the insertion device on the desired application site on the body of the patient such that the infusion cannulas and puncturing tips of the insertion head can penetrate correctly into the body during the subsequent insertion movement.

In a fifth step, the insertion movement of the insertion head is triggered or initiated, whereby the insertion head is separated from the retention means at the start of the insertion movement, or slightly thereafter, such that it executes at least part or the greatest part of the insertion movement free of the retention means.

This method for applying an insertion head to the body of a patient using an insertion device permits a short insertion phase with a correspondingly short pain interval, and irritation of the puncture site upon release of the insertion head from the insertion device can be reliably avoided, and at the same time the method is easier to carry out compared to methods of this type known today.

In a preferred embodiment of the method, the insertion head is held in the first position by the retention means purely with a force fit, purely with a form fit, or with a combination of a force fit and form fit. Particularly in the case of a purely force fit, this affords the advantage that, at the start of the insertion movement, the insertion head can easily be knocked out of the retention means by a thrust element of the drive means and is thus detached from said retention means. It may be preferred in this connection that, after being engaged into the retention means, the insertion head is held in the engage position by the retention means with a purely form fit or with a combination of a force fit and form fit. In some embodiments, it is preferred that the form fit is cancelled during the movement of the retention means, with the insertion head held therein, from the engage position to the standby position.

Alternatively, in some embodiments, it is preferred that, after it has been engaged into the retention means, the insertion head is held in the engage position by the retention means purely with a force fit, and the force fit is reduced during the movement of the retention means, with the insertion head held therein, from the engage position to the standby position. Embodiments are also provided, however, in which the insertion head is held by the retention means purely with a force fit both in the engage position and also in the standby position, in each case with a force fit of the same strength.

In those method variants in which a form fit is cancelled or a force fit is reduced during the movement of the retention means, with the insertion head held therein, from the engage position to the standby position, an advantage, especially when using insertion heads with fixed infusion cannulas or puncturing tips, is that the insertion head is held more firmly in the engage position than in the standby position, with the result that the needle guard or cannula guard can be removed without any danger of the insertion head coming loose again from the retention means.

In another preferred embodiment of the method, the retention means are held unmoved relative to the contact face, at least during a large part of the insertion movement or during the entire insertion movement. This has the advantage that inexpensive and structurally simple insertion devices according to the present invention can be used for carrying out the method.

In another preferred embodiment of the method, the retention means, with the insertion head held thereon, can be brought manually by muscle force from the engage position to the standby position, e.g. by displacing a slide element, turning a rotary knob or pressing a push button. Such maneuvers are especially suitable for imparting to the insertion device the force necessary for pretensioning the energy-storing element and displacing the retention means.

In yet another preferred embodiment of the method, the energy-storing element is made ready in the pretensioned state, and the insertion movement is then triggered by actuation of an actuation member or by simultaneous or sequential actuation of several actuation members. This favors a controlled application process.

In some preferred embodiments, arranging the insertion device on the body of the patient and triggering the insertion movement is done with one hand, such that areas that are difficult to reach or can be reached with only one hand are also accessible for the application.

In yet another preferred embodiment of the method according to the present invention, an insertion head with at least one deployable infusion cannula and/or at least one deployable puncturing tip, and in a state in which all the deployable infusion cannulas and puncturing tips of the insertion head are folded inwardly, is engaged into the retention means. All the deployable infusion cannulas and puncturing tips of the insertion head are then deployed during the movement of the retention means, with the insertion head held correctly therein, from the engage position to the standby position. The insertion head is then ready for application. In this way, the danger of the user sustaining an injury when preparing for the application can be reduced or practically eliminated.

DETAILED DESCRIPTION

With regard to fastening, mounting, attaching or connecting components of the present invention, unless specifically described as otherwise, conventional mechanical fasteners and methods may be used. Other appropriate fastening or attachment methods include adhesives, welding and soldering, the latter particularly with regard to the electrical system of the invention, if any. In embodiments with electrical features or components, suitable electrical components and circuitry, wires, wireless components, chips, boards, microprocessors, inputs, outputs, displays, control components, etc. may be used. Generally, unless otherwise indicated, the materials for making the invention and/or its components may be selected from appropriate materials such as metal, metallic alloys, ceramics, plastics, etc.

Figure 1:
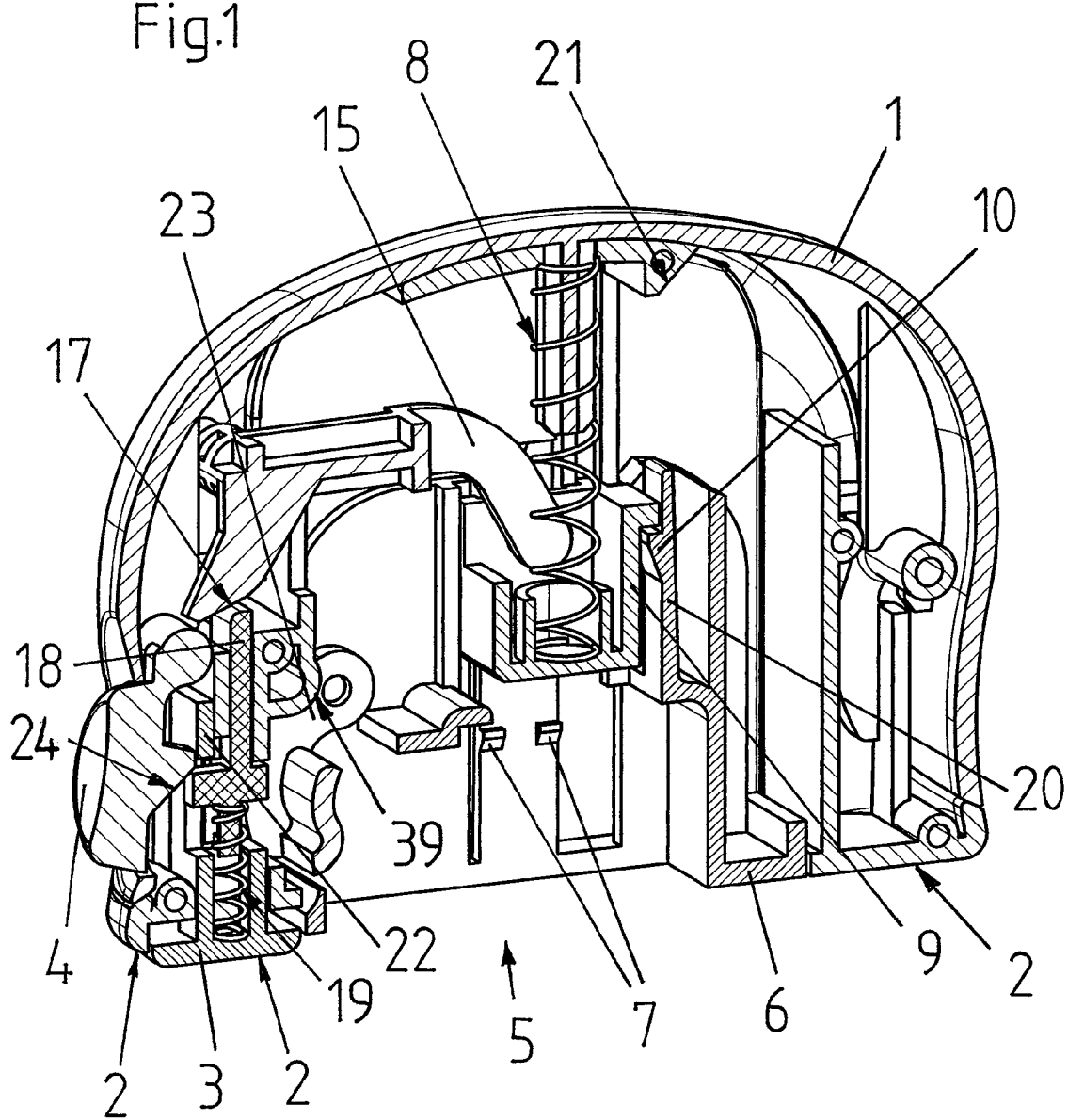
FIG. 1 is a vertical section through a first embodiment of the insertion device according to the present invention, in the non-pretensioned state and without an insertion head.

A first embodiment of the insertion device according to the present invention, for insertion heads with deployable infusion cannula, is shown in vertical section in FIG. 1, in the non-pretensioned state and without an insertion head. As can be seen, the insertion device has a portal-like housing 1 which, on its underside, has contact faces 2 via which the insertion device is placed and pressed onto the body of a patient for application of an infusion set using the insertion device. One of the contact faces 2 is formed by a securing button 3, which protrudes or extends downwardly from the underside of the housing 1 and which, to release the insertion device, when the latter is in a state ready for application or use by being placed and pressed onto the body of the patient, can be displaced into a release position in which the contact face 2 of the securing button 3 is essentially flush with that surface of the contact face 2 of the housing 1 adjoining the securing button 3.

The insertion device also has a trigger knob 4 with which the insertion movement for applying the insertion head to the body of the patient can be triggered or initiated when the insertion device is in a state ready for use and the securing button 3 is arranged in the release position. The securing button 3 and trigger knob 4 thus represent two actuation members which have to be actuated simultaneously in order to trigger the insertion movement.

As can be seen here, the insertion device, in the situation shown in FIG. 1, has, on its underside, a receiving aperture 5 which is formed by a slide element 6 and in which projections 7 are mounted which are resilient under the effect of the slide element 6 and with which an infusion set to be applied can be held in the receiving aperture 5, in the present case exclusively with a force fit.

As can also be seen, the insertion device comprises, as a driver or drive means, a helical spring 8 which acts on a hammer element 9 which, in the situation shown, bears on a catch projection 10 of the slide element 6.

Figure 2:
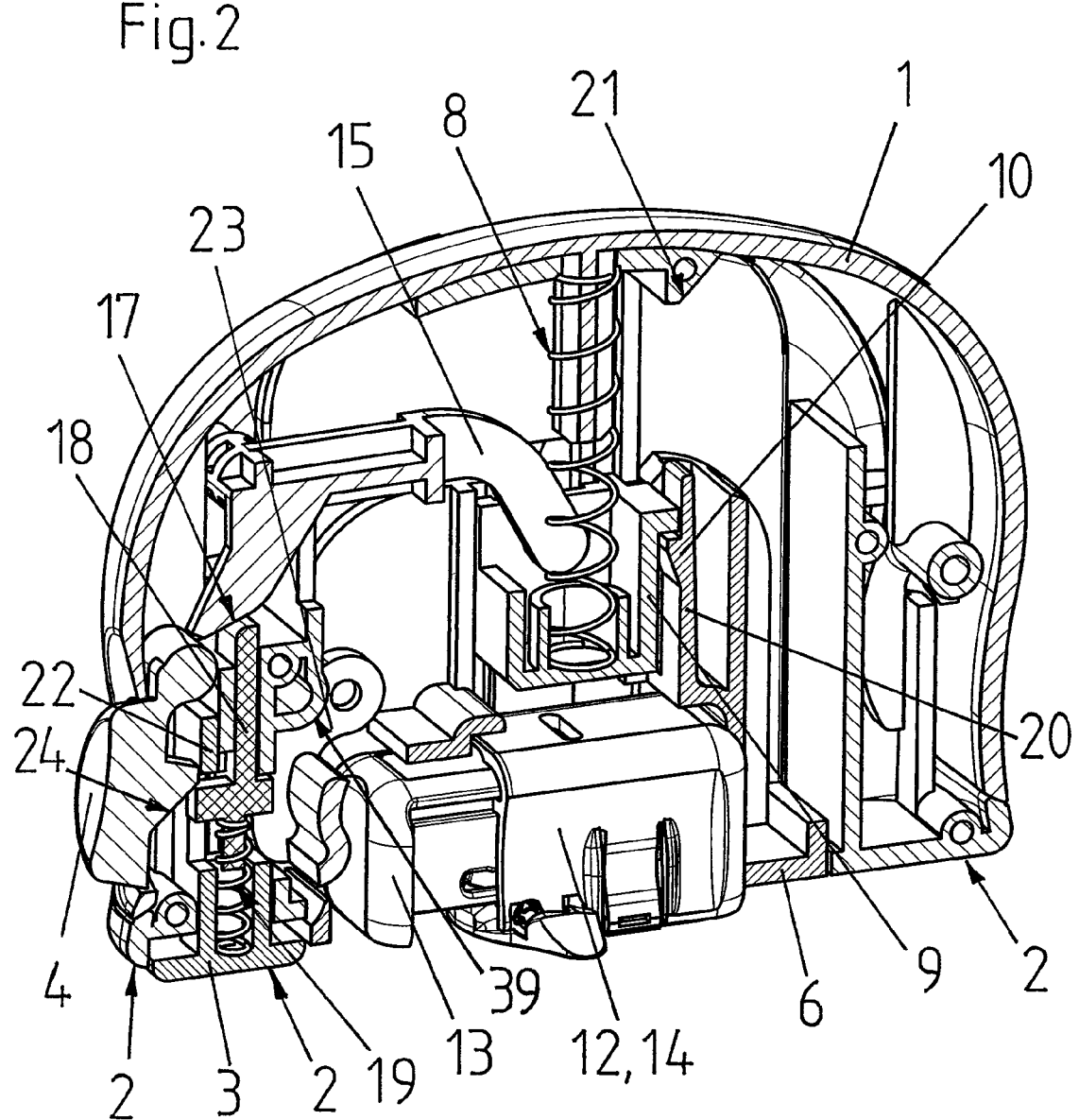
FIG. 2 is a view of the insertion device of FIG. 1, but with an insertion head arranged in it.
Figure 3:
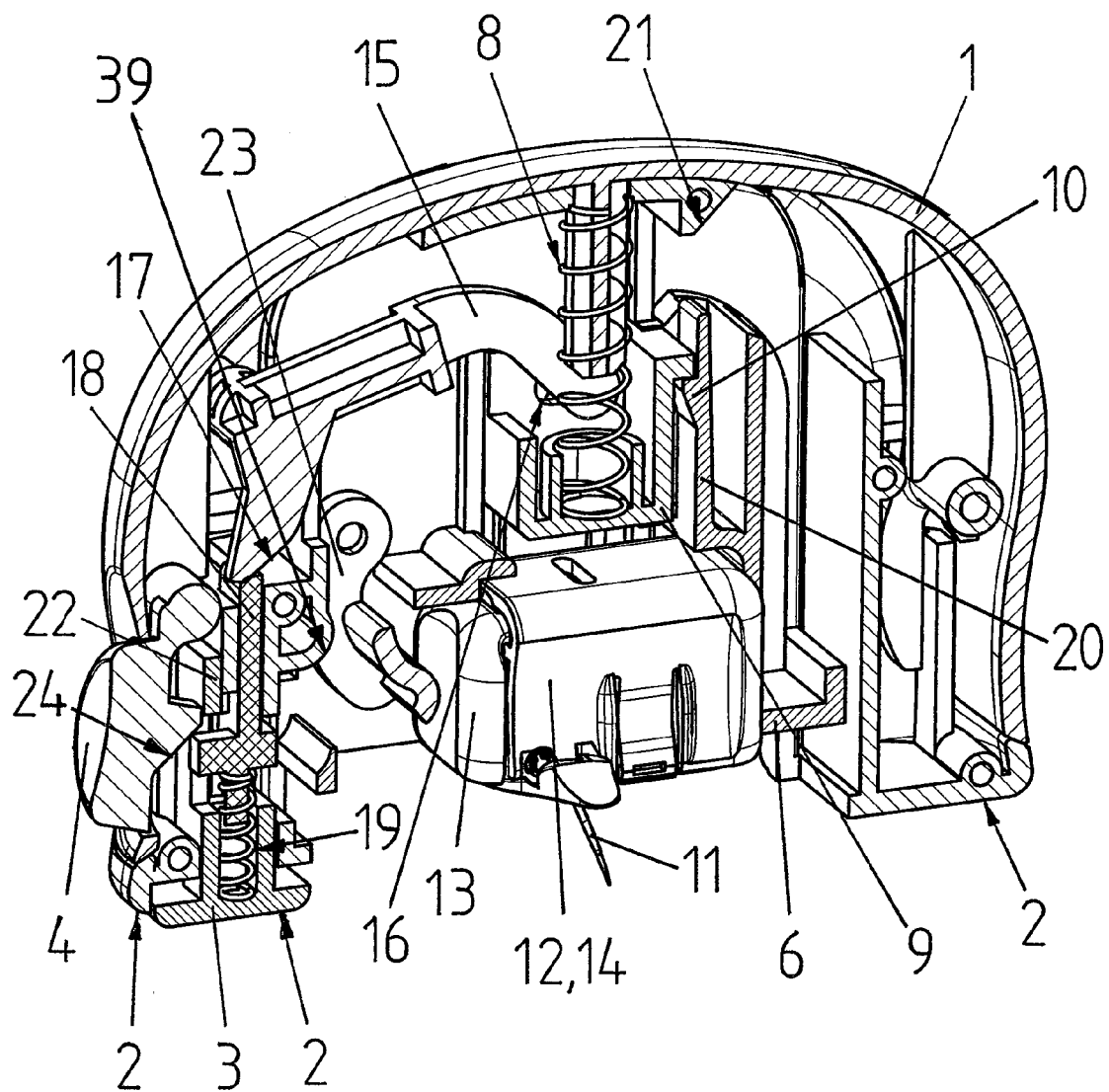
FIG. 3 is a vertical section through the insertion device of FIGS. 1 and 2, during pretensioning, and with the insertion head arranged in it.
Figure 4:
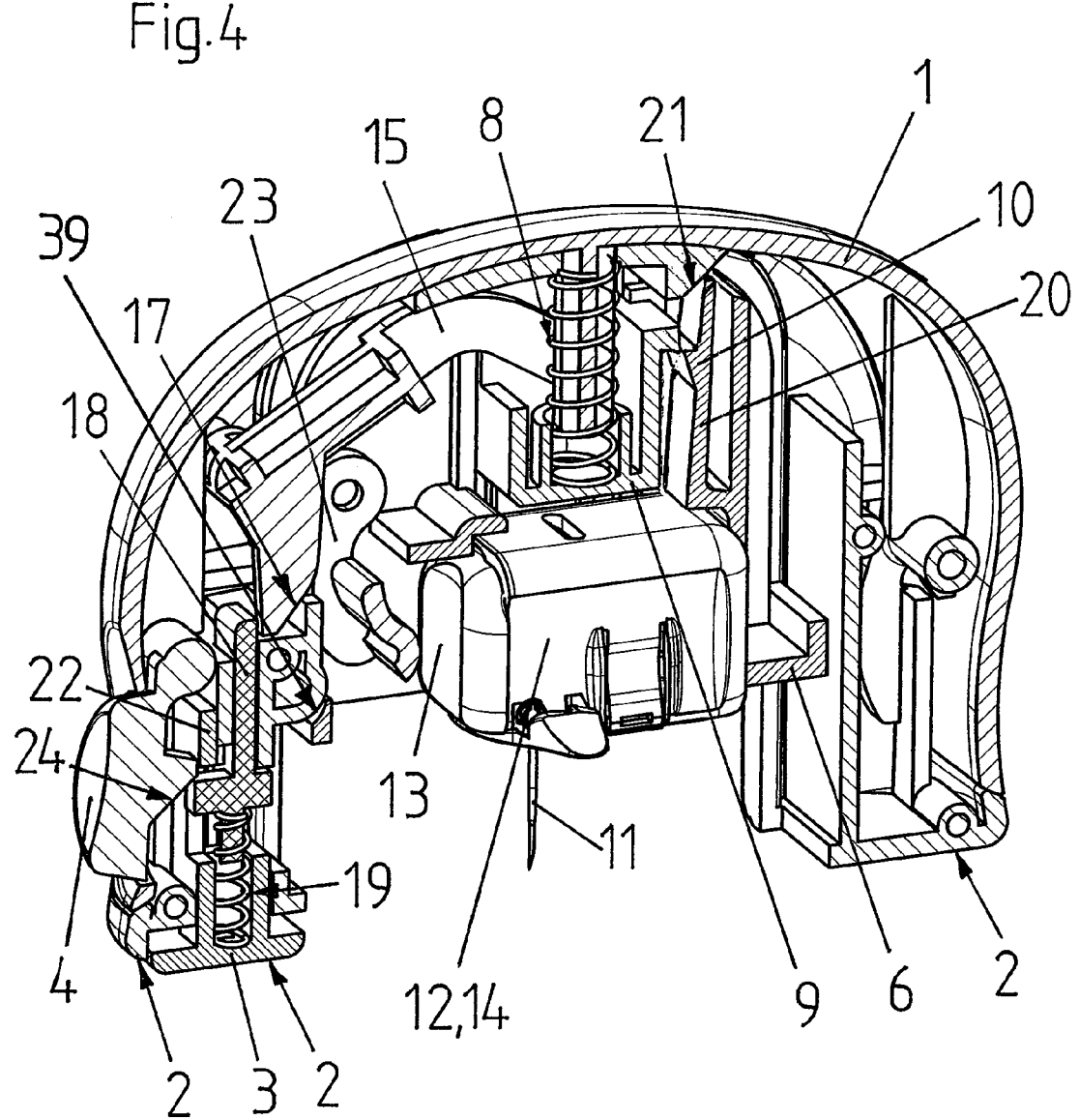
FIG. 4 is a vertical section through the insertion device of the preceding figures, in the pretensioned state and with an insertion head arranged therein in the secured state ready for application.

As can be seen from a comparison with FIGS. 2, 3 and 4, which show the insertion device in the state as before, but with an insertion head 12 engaged into the receiving aperture (FIG. 2), during pretensioning with the insertion head 12 held therein (FIG. 3), and in the pretensioned and secured state ready for application or use (FIG. 4), to effect pretensioning and at the same time to deploy the infusion cannula 11 of the infusion set 12, the housing 1 is gripped with one hand and the slide element 6 is gripped with the other hand and, with the infusion set 12 held therein, is moved upwards relative to the housing 1, entraining the hammer element 9 with it and resulting in increased pretensioning of the helical spring 8. Since the slide element 6, in its upward movement, only frees the portal opening of the housing 1, and in its uppermost position does not protrude above or extend beyond the top edge of the housing 1, the overall dimensions of the insertion device remain unchanged.

At the same time, the cannula 11 of the insertion head 12 is deployed, by an actuation lever 23 mounted pivotably on the slide element 6 running on or moving along a control ramp 39 in the housing 1 and being pivoted toward the insertion head 12, thus pushing the left-hand housing part 13 of the insertion head 12, which forms a displaceable actuation member of the insertion head 12, into the right-hand housing part 14 and thus deploys the cannula 11 via a mechanism (not shown) located in the interior of the insertion head. The insertion heads 12 shown in the illustrative embodiments are exclusively infusion sets for insulin, which, in the states shown here prior to application, have a flexible cannula (soft cannula) supported by a puncture needle that is to be removed following the application. (It should be understood that the present invention may be adapted for use with infusion sets suitable for use with other substances, or for use with other infusion sets.) For the purposes of explaining the present invention, however, a distinction does not have to be made here between puncture needle and flexible cannula, for which reason both are each together designated as "cannula 11".

Simultaneous with the movement of the insertion head 12 with the slide element 6 from the receiving position shown in FIG. 2 to the standby position shown in FIG. 4 in which the insertion head 12 is located in the claimed first position, a trigger lever 15, which is designed as a double lever and is guided at its first end with a guide cylinder (not shown), like a guide block, in a horizontal oblong hole 16 on the rear face of the hammer element 9, is pivoted about a bearing point in the housing 1, whereby a run-up ramp 17 formed at its second end moves a latch element 18 downwardly counter to the force of a locking spring 19 until it extends past the latch element 18 and then is locked in the situation shown in FIG. 4 by the latch element 18 shooting or moving back under the force of the spring. Correspondingly, the hammer element 9 in this situation is held by the trigger lever 15 in the upper position shown in FIG. 4, counter to the force of the pretensioned spring 8.

As soon as the trigger lever 15 is locked by the latch element 18, the catch projection 10, which entrains the hammer element 9 with it, is disengaged from the hammer element 9, since the spring shackle 20 of the slide element 6 carrying the catch projection 10 runs or moves with its free end on a ramp surface 21 in the housing 1, such that the shackle 20 is bent away from the hammer element 9. In this state, in which the slide element 6 is pushed up to the maximum extent, it locks reversibly on the housing 1 via a catch or catch means (not shown) such that it can be moved in the opposite direction, and back into the engage position, only after overcoming a high initial resistance. Suitable catch means are known to a person skilled in the art and could be formed, for example, by a lug held on a spring tongue and engaging with a run-on bevel in an undercut such that the locked connection can be released again by deflection of the spring tongue under increased force, by the run-on bevel running onto an edge of the undercut.

Figure 5:
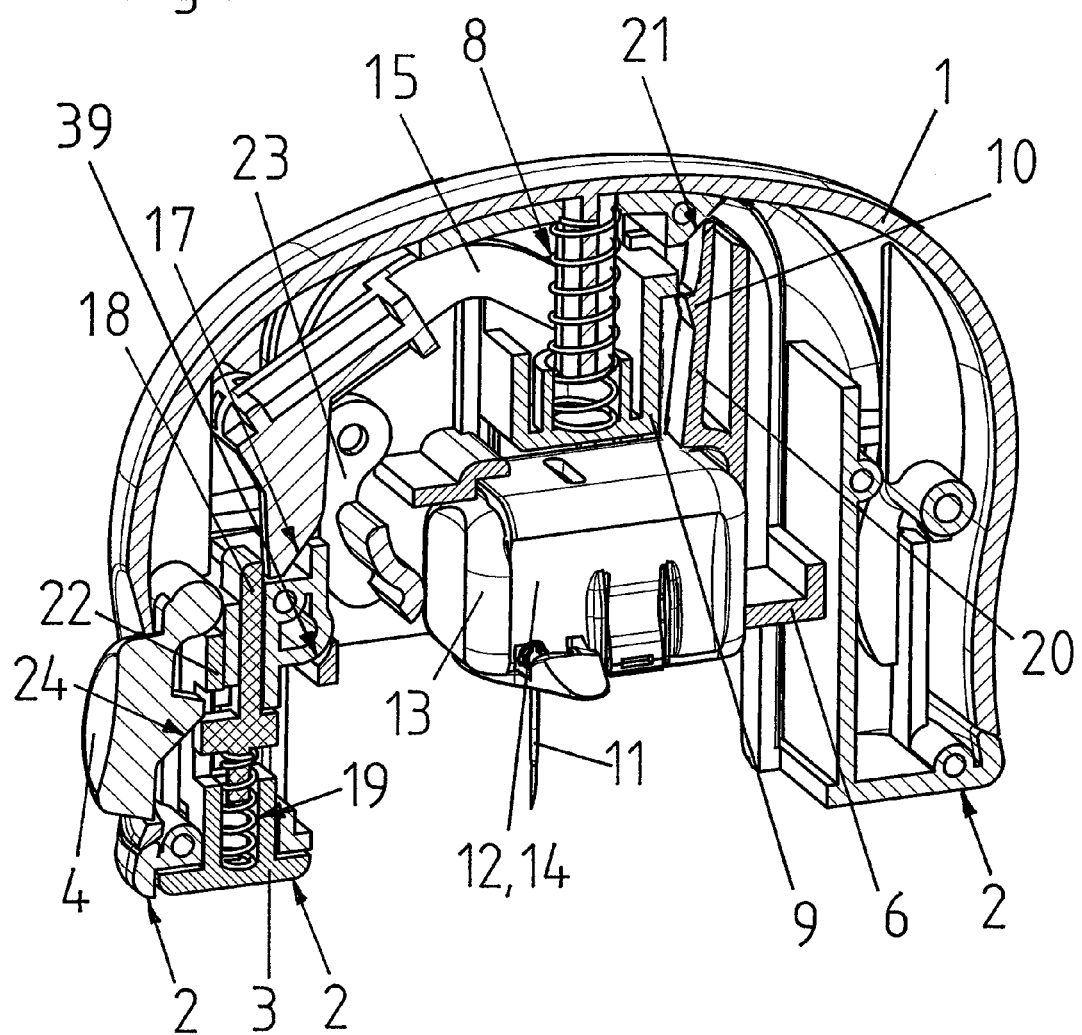
FIG. 5 is a view of the insertion device of FIG. 4, but in the released state.

As will be seen from a comparison of FIGS. 4 and 5, which show the insertion device in the state ready for application or use, on the one hand in the secured state (FIG. 4) and on the other hand in the released state (FIG. 5), the securing button 3, on which the locking spring 19 bears via its end directed away from the latch element 18, forms a securing slide 22 in the housing 1, which securing slide 22, in the situation shown in FIG. 4, has a form fit and prevents actuation of the trigger knob 4. Only when a pressure force is exerted on the securing button 3 counter to the direction of force of the locking spring 19, for example by pressing the insertion device onto the application site on the body of a patient, can it be pushed so far into the housing 1 that its underside bearing a contact face 2 is essentially flush with the contact face 2 of the housing 1 adjoining it. In this position, which is shown in FIG. 5, the securing slide 22 frees the trigger knob 4.

Figure 6:
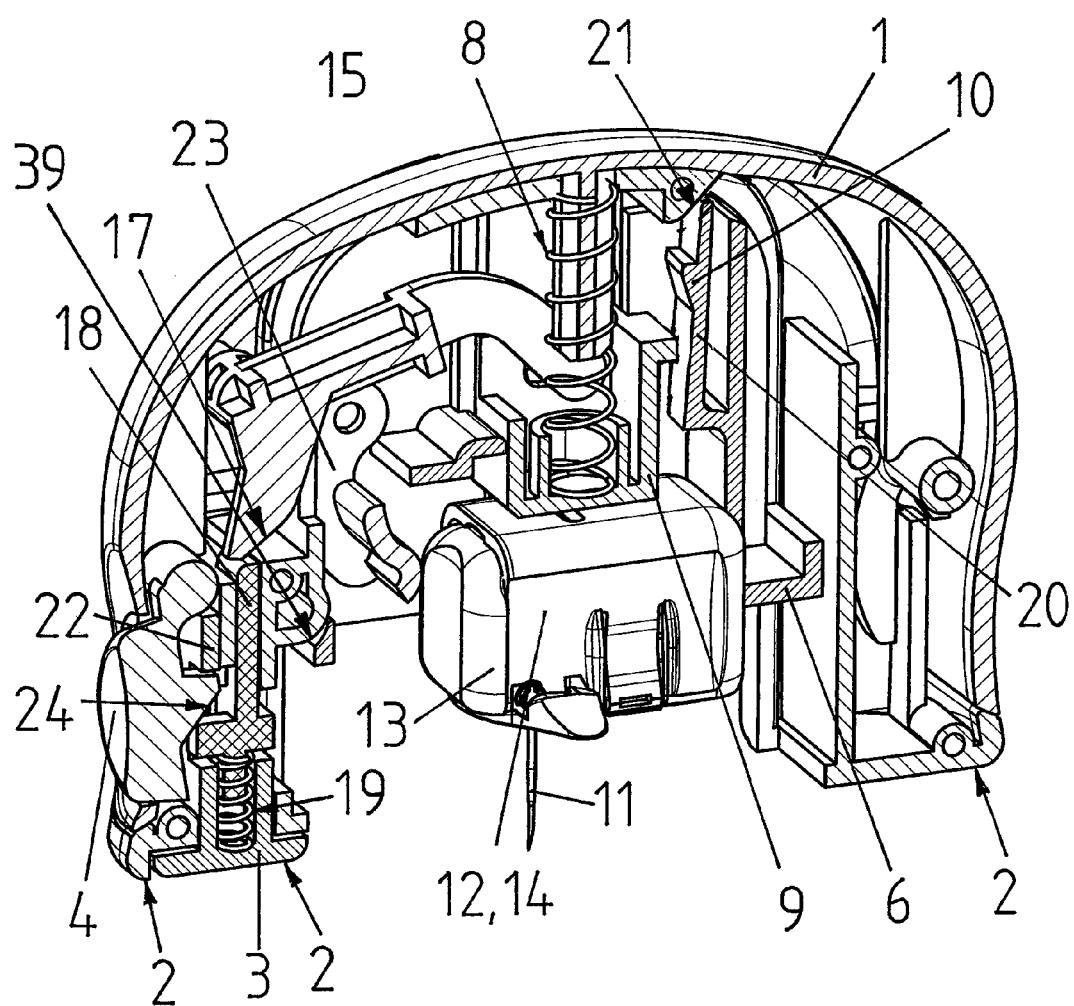
FIG. 6 is a view of the insertion device of FIG. 5, but shortly after the actuation of the trigger button.

As can be seen from FIG. 6, which shows the insertion device shortly after actuation of the trigger knob 4, the trigger knob 4 has, on its face directed toward the interior of the housing 1, a trigger ramp 24 which, upon actuation of the trigger knob 4, is moved along a control edge of the latch element 18 and thus draws the latter downwardly counter to the force of the locking spring 19, as a result of which the locked second end of the trigger latch 15 is freed and the hammer element 9 held at the first end thereof shoots downwardly, driven by the force of the pretensioned helical spring 8. The hammer element 9 strikes the top face of the insertion head 12 held with a force fit in the first position in the slide element 6, releases the insertion head 12 from the catch projections 7 and drives it down for application or placement of the insertion head 12 on the body of a patient, with the cannula 11 penetrating into the body ahead of it, until the cannula 11 is completely inserted and the insertion head 12 lies with its underside on the surface of the body. The slide element 6 with the catch projections 7 remains unmoved relative to the housing 1 and, for application of a further insertion head 12, first has to be brought back to the engage position, by being moved downwardly relative to the housing 1 after overcoming an initially high resistance.

After the application, the applied insertion head 12 is completely separated from the insertion device, such that the latter can be removed without causing any irritation of the application site.

Figure 7:
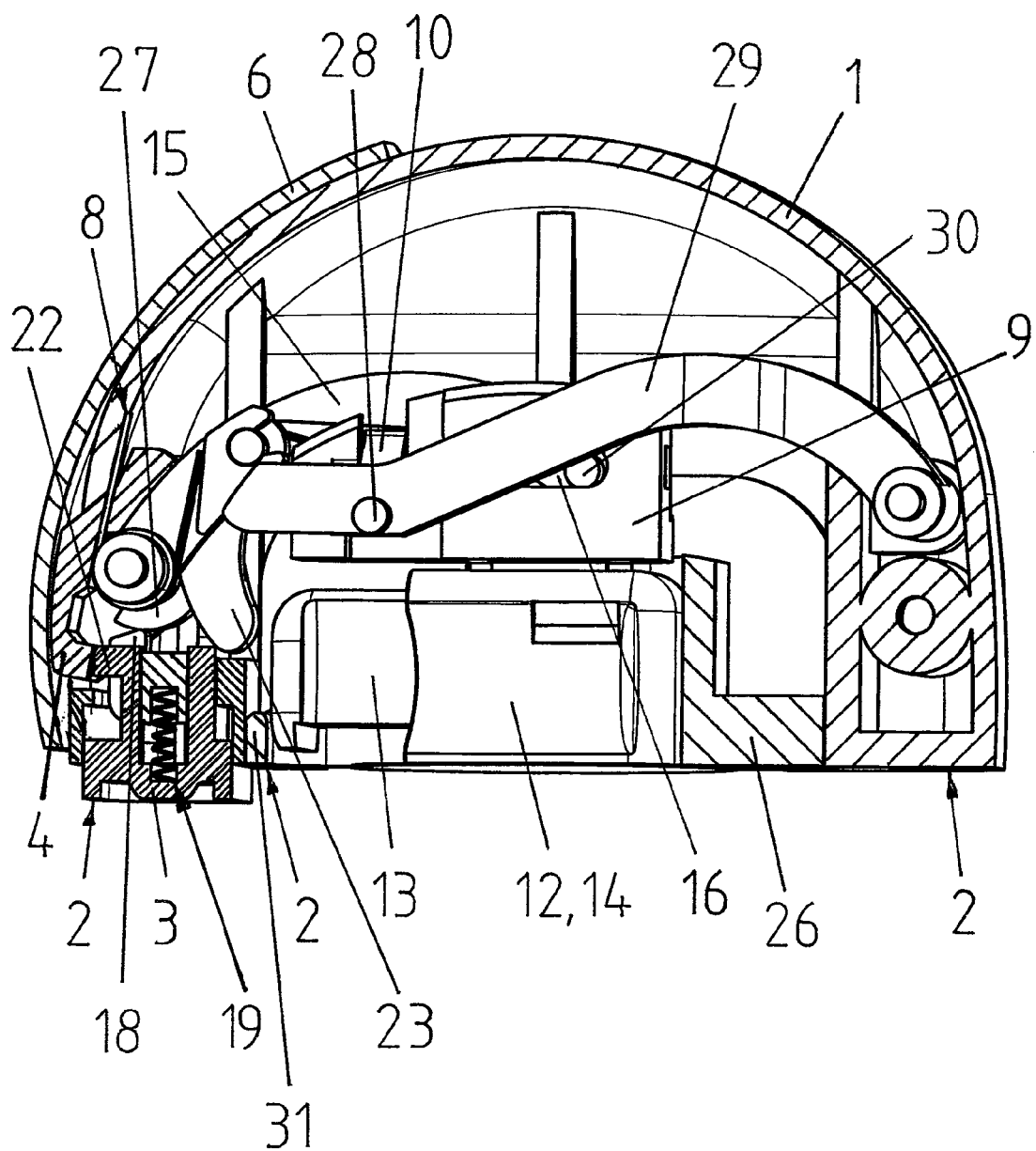
FIG. 7 is a vertical section through a second embodiment of the insertion device according to the present invention, in the non-pretensioned state and with an insertion head arranged therein.
Figure 8:
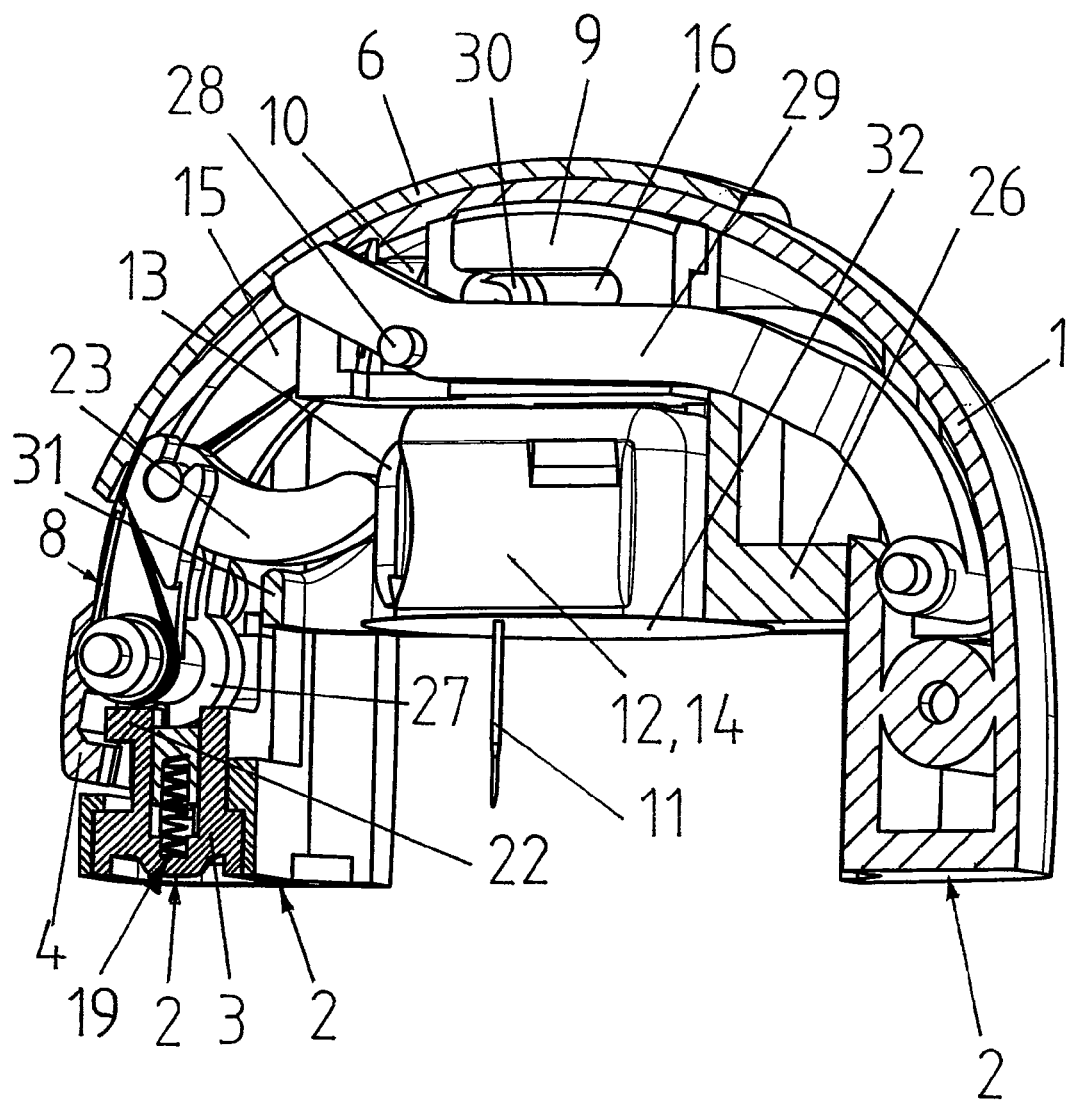
FIG. 8 is a vertical section through the insertion device of FIG. 7, in the pretensioned and released state.

A second embodiment of the insertion device according to the present invention, likewise for an infusion set with deployable infusion cannula, is shown in vertical section in FIGS. 7 and 8, on the one hand in the non-pretensioned state with an insertion head already engaged in it (FIG. 7) and on the other hand in the pretensioned and released state with an infusion set arranged ready for application in the first position (FIG. 8).

As will be seen, this insertion device too comprises a portal-like housing 1 which, on its underside, has contact faces 2 via which the insertion device is placed and pressed onto the body of a patient for application or placement of an infusion set using the insertion device. Part of the contact faces 2 is formed by a securing button 3, which protrudes downwardly from the underside of the housing 1 and which, to release the insertion device, when the latter is in a state ready for application or use by being placed and pressed onto the body of the patient, can be displaced into a release position in which the contact face 2 of the securing button 3 is essentially flush with the contact face 2 of the housing 1 adjoining the securing button 3 (see FIG. 8).

The insertion device also has a trigger knob 4 with which the insertion movement for applying the insertion head to the body of the patient can be triggered when the insertion device is in the state shown in FIG. 8. The securing button 3 and trigger knob 4 thus also in this case represent two actuation members 3, 4, which have to be actuated simultaneously to trigger or initiate the insertion movement.

This insertion device too, in the relaxed state without insertion head (as in FIG. 7, but without an engaged infusion set), has, on its underside, a receiving aperture which is formed by a receiving element 26 mounted vertically displaceably in the housing 1 and in which projections (not shown) are mounted which are resilient under the effect of the receiving element 26 and with which the infusion set 12 is held in the receiving aperture, exclusively with a force fit in both of the situations shown.

As can also be seen, the insertion device comprises, as at least a part of a driver or drive means, a torsion spring 8 which acts on a hammer element 9 via a trigger lever 15. The trigger lever 15 is mounted so as to rotate about the rotation centre of the torsion spring 8 in the housing and has, at its end remote from the rotation centre, a guide cylinder 30 which, like a sliding block, is guided in a horizontal oblong hole 16 in the hammer element 9.

To effect pretensioning and at the same time to deploy the infusion cannula 11 of the infusion set 12 held in the receiving element 26, the housing 1 is gripped with one hand, and a slide element 6 displaceable along the outer contour of the housing 1 is gripped with the other hand, and the slide element 6 is then displaced from the position shown in FIG. 7 to the position shown in FIG. 8. It is likewise possible for the slide element 6 to be operated using the same hand with which the housing 1 is held.

Because they are sectional views, the figures do not show how, during the displacement of the slide element 6, a guide (not shown) formed by the latter is guided along a guide cylinder 28 of a tension lever 29, as a result of which the tension lever 29 is guided upwardly. On the rear face, the tension lever 29 has, lying opposite the guide cylinder 28, a further cylinder (not visible) which engages under a detent 10 mounted in the hammer element 9. During its upward movement, the tension lever 29 carries the hammer element 9 up with it via the cylinder and the detent 10, which hammer element 9 in turn entrains the trigger lever 15 upwardly from the position shown in FIG. 7 to the position shown in FIG. 8, counter to the force of the pretensioned spring 8 and with increasing pretensioning of the latter. In so doing, the cylinder of the tension lever 29 slides horizontally along the underside of the detent 10, until, at the end of the pretensioning movement, it is arranged next to the detent 10, that is to say disengaged from the detent 10.

As can be seen from FIG. 7, the trigger lever 15 has, at its end forming the rotation centre, a locking element 27 which, during its pivoting movement, is guided in a sliding movement along a latch element 18 acted upon by the force of a locking spring 19, until it extends past the latch element 18 and is then locked by the latter in the pretensioned situation shown in FIG. 8. This locking takes place shortly before the cylinder of the tension lever 29 disengages from the detent 10. After the disengagement of the cylinder from the detent 10, the hammer element 9 is held by the trigger lever 15 in the upper position shown in FIG. 8.

During its upward movement, the hammer element 9 also entrains the slide element 26, which in turn, by a carrier lug 31 formed by it, entrains an activation lever 23 that is mounted rotatably on the trigger lever 15 counter to the force of an auxiliary spring. The activation lever 23 is pivoted towards the insertion head 12, thus pushing the left-hand housing part 13 of the insertion head 12, which forms a displaceable actuation member of the insertion head 12, into the right-hand housing part 14 and thus deploying the cannula 11 via a mechanism (not shown) located in the interior of the insertion head.

Shortly before the cylinder of the tension lever 29 disengages from the detent 10, the slide element 26, in the position shown in FIG. 8, locks reversibly on the housing 1 with catch means (not shown) such that it can be moved in the opposite direction, and back to the engage position, only after overcoming a high initial resistance. Suitable catch means are known to a person skilled in the art and could also be formed here, for example, by a lug held on a spring tongue and engaging with a run-on bevel in an undercut, such that the locked connection can be released again by deflection of the spring tongue under increased force, by the run-on bevel running onto an edge of the undercut.

As will be seen from a comparison of FIGS. 7 and 8, the securing button 3, on which the locking spring 19 bears via its end directed away from the latch element 18, forms a securing slide 22 in the housing 1, which securing slide 22, in the situation shown in FIG. 7, has a form fit and prevents actuation of the trigger knob 4. Only when a pressure force is exerted on the securing button 3 counter to the direction of force of the locking spring 19, for example by pressing the insertion device onto the application site on the body of a patient, can it be pushed so far into the housing 1 that its underside bearing a contact face 2 is essentially flush with the contact face 2 of the housing 1 adjoining it. In this position, which is shown in FIG. 8, the securing slide 22 frees the trigger knob 4.

In this embodiment too, the trigger knob 4 has, on its face directed toward the interior of the housing 1, a trigger ramp (not visible) which, upon actuation of the trigger knob 4, is moved along a control edge of the latch element 18 and thus draws the latter downwardly counter to the force of the locking spring 19, as a result of which the locking element 27 of the trigger lever 15 is freed and the hammer element 9 held at the first end thereof shoots or moves downwardly, driven by the force of the pretensioned torsion spring 8. The hammer element 9 strikes the top face of the insertion head 12 held with a force fit in the first position in the slide element 6, releases the insertion head 12 from the catch projections and drives it down for application or placement of the insertion head 12 to the body of the patient, with the cannula 11 penetrating into the body ahead of it, until the cannula 11 is completely inserted and the insertion head 12 lies with its underside, which is formed by an adhesive pad 32, on the surface of the body. The receiving element 26 remains unmoved relative to the housing 1 and, for application of a further insertion head 12, first has to be brought back to the engage position. For this purpose, the slide 6 is brought back into the position shown in FIG. 7, where it again entrains the tension lever 29 downwardly, which tension lever 29 in turn unlocks the receiving element 26 from the housing 1 by overcoming an initially high resistance and then carries it into the position shown in FIG. 7. During the downward movement of the tension lever 29, the cylinder (not visible) arranged on its rear face runs across the detent 10, forces the latter temporarily back counter to the force of a detent spring (not shown) and then locks under this again. In this state, a further infusion set can be engaged in the recess of the receiving element 26.

Figure 9:
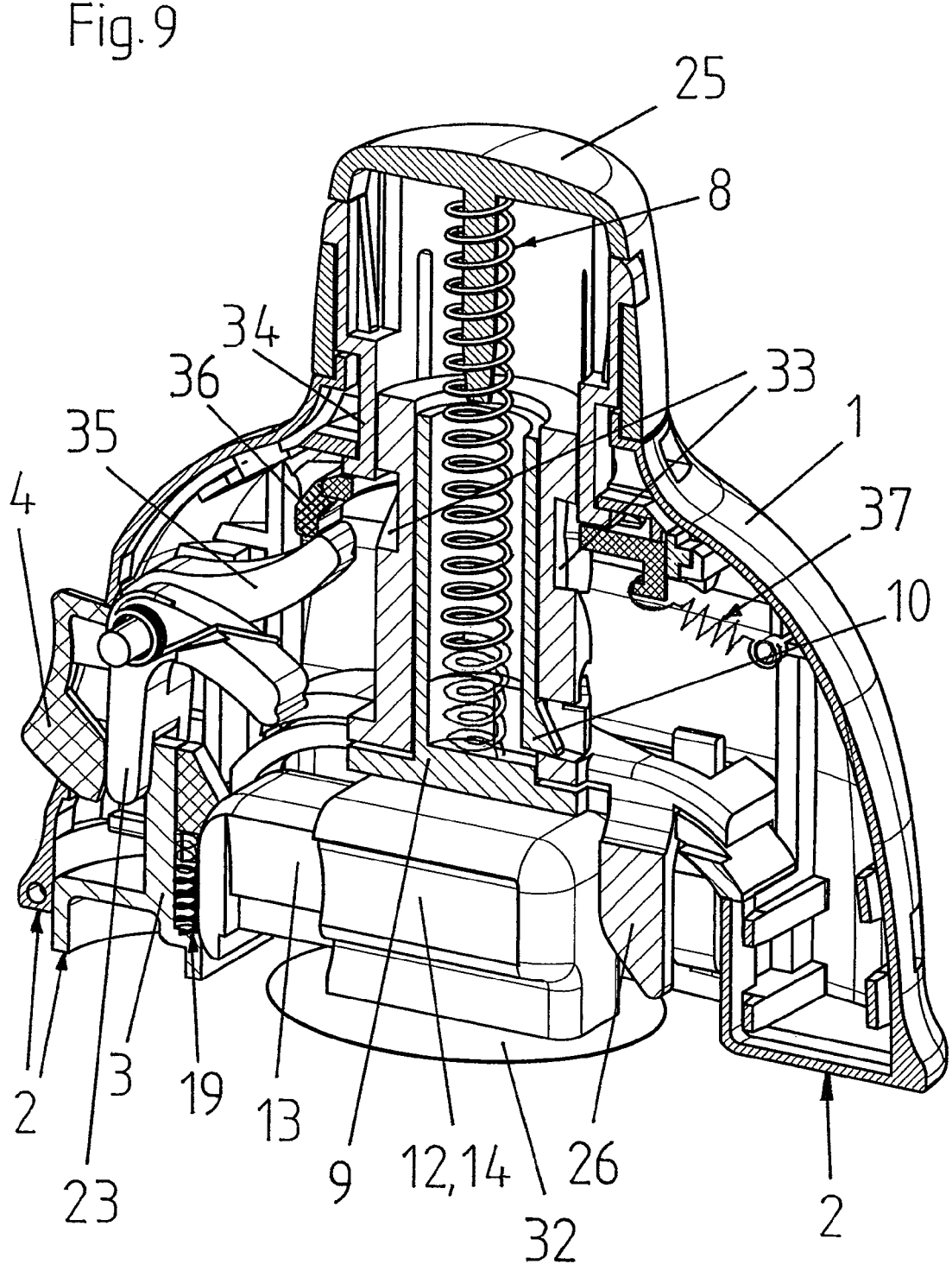
FIG. 9 is a vertical section through a third embodiment of the insertion device according to the present invention, in the non-pretensioned state, with an insertion head arranged therein.
Figure 10:
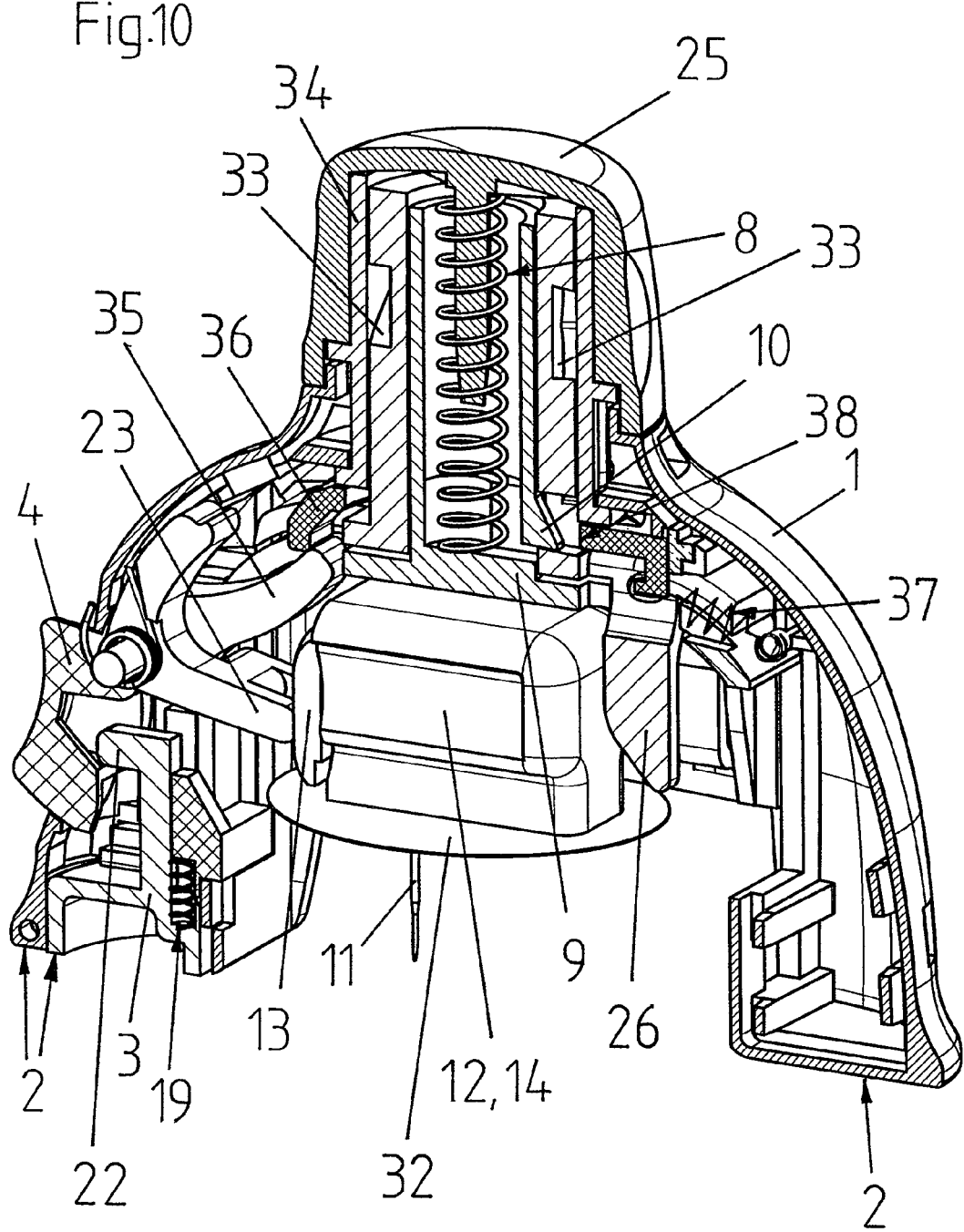
FIG. 10 is a vertical section through the insertion device of FIG. 9, in the pretensioned and released state.

A third embodiment of the insertion device according to the present invention, likewise for an infusion set with deployable infusion cannula, is shown in vertical section in FIGS. 9 and 10, on the one hand in the non-pretensioned state with an insertion head already engaged in it (FIG. 9) and on the other hand in the pretensioned and released state with an infusion set arranged ready for application therein in the claimed first position (FIG. 10).

As will be seen, this embodiment of an insertion device in accordance with the present invention comprises a portal-like housing 1 which, on its underside, has contact faces 2 via which the insertion device is placed and pressed onto the body of a patient for application of an infusion set using the insertion device. One of the contact faces 2 is again formed by a securing button 3, which, as in the two exemplary embodiments already described above, protrudes or extends downwardly from the underside of the housing 1 and which, in order to release the insertion device, when the latter is in a state ready for application by being placed and pressed onto the body of the patient, can be displaced into a release position in which the contact face 2 of the securing button 3 is essentially flush with the contact face 2 of the housing 1 adjoining the securing button 3 (see FIG. 10).

The insertion device in this case also has a trigger knob 4 with which the insertion movement for applying the insertion head to the body of the patient can be triggered or initiated when the insertion device is in the state according to FIG. 10. The securing button 3 and trigger knob 4 thus also in this case represent two actuation members 3, 4, which have to be actuated simultaneously to trigger the insertion movement.

This insertion device too, in the non-pretensioned state without insertion head (as in FIG. 9, but without an engaged infusion set), has, on its underside, a receiving aperture which is formed by a receiving element 26 mounted vertically displaceably in the housing 1 and in which retention means (not shown) formed by the receiving element 26 are arranged, with which the infusion set 12 is held in the receiving aperture with a force fit.

As can also be seen, the insertion device, like the first embodiment described, comprises, as a drive means, driver or portion thereof, a helical spring 8 which acts directly on a hammer element 9 which, in the situations shown, bears with a catch projection 10 on the receiving element 26. The helical spring 8 is surrounded coaxially by substantially cylindrically shaped sections of the hammer element 9 and of the receiving element 26. On its outer circumference, the cylindrical section of the receiving element 26 has guides 33 in which slide blocks (not visible) of a rotary sleeve 34 surrounding this section of the receiving element 26 engage. The rotary sleeve 34 is in turn mounted rotatably in the housing 1, but is axially immovable relative to the force direction of the spring 8, and it carries a rotary knob 25, with the helical spring 8 bearing on the inner face of the latter.

To effect pretensioning and at the same time to deploy the infusion cannula 11 of the infusion set 12 held in the receiving element 26, the housing 1 of the insertion device located in the state according to FIG. 9 is gripped with one hand, and the rotary knob 25 is turned through approximately 120° with the other hand, which leads to a corresponding turning of the rotary sleeve 34 relative to the housing 1. In this way, its slide blocks are displaced inside the guides 33 of the receiving element 26 and, as a result, the receiving element 26, with the infusion set 12 held therein, is lifted from the position shown in FIG. 9 to the position shown in FIG. 10, with the hammer element 9 being entrained, and with corresponding increased pretensioning of the helical spring 8. On reaching its rotation position, which corresponds to the maximally pretensioned situation of the insertion device shown in FIG. 10, the rotary knob 25 in this rotation position locks reversibly on the housing 1 via catch means (not shown) such that it can be turned further, or turned in the opposite direction, only when a high initial resistance is overcome. Suitable catch means are known to a person skilled in the art and could also be formed, for example, by a lug held on a spring tongue and engaging with a run-on bevel in an undercut, such that the locked connection can be released again by deflection of the spring tongue under increased force, by the run-on bevel running onto an edge of the undercut.

Since, when it moves upwards, the retention element 26 only frees the portal opening of the housing 1, and remains inside the housing 1, the overall dimensions of the insertion device remain unchanged in this case too, in the same way as in the first embodiment of the insertion device according to the present invention.

At the same time as the rotary knob 25 is turned and the internal components 8, 9, 26, 34 are thus moved, the cannula 11 of the insertion head 12 is deployed by means of one of the two arms of an activation lever 23, mounted in the housing 1 and designed as a double lever, being entrained by the receiving element 26 (not visible because of the sectional depiction) and, in this way, its second arm is pivoted toward the insertion head 12, thus pushing the left-hand housing part 13 of the insertion head 12, which forms a displaceable actuation member of the insertion head 12, into the right-hand housing part 14 and thus deploying the cannula 11 via a mechanism (not shown) located in the interior of the insertion head.

As will be seen from a comparison of FIGS. 9 and 10, the securing button 3 is forced out by the force of a spring 19 and forms, in the housing 1, a securing slide 22 which, in the situation shown in FIG. 9, prevents actuation of the trigger knob 4. Only when a pressure force is exerted on the securing button 3 counter to the direction of force of the spring 19, for example by pressing the insertion device onto the application site on the body of a patient, can it be pushed so far into the housing 1 that its underside bearing a contact face 2 is essentially flush with the contact face 2 of the housing 1 adjoining it. In this position, which is shown in FIG. 10, the securing slide 22 frees the trigger knob 4.

The trigger knob 4 is mounted pivotably about the rotation axis of the activation lever 23 in the housing 1 and forms, inside the housing 1, a trigger lever 35 which runs or moves on a control edge of a trigger slide 36 mounted horizontally displaceably and axially non-displaceably in the housing 1 relative to the force direction of the drive spring 8, such that an actuation of the trigger button 4 displaces the trigger slide 36 to the left counter to the force of a restoring spring 37.

In this way, with the insertion device pretensioned (FIG. 10), the catch projection 10, with which the hammer element 9 acted upon by the force of the helical spring 8 bears on the receiving element 26, is forced toward the left and in doing so disengages from the receiving element 26, such that the hammer element 9 moves downwardly, driven by the force of the spring 8 and guided within the cylindrical section of the retention element 26. The hammer element 9 strikes the top face of the insertion head 12 held with a force fit in the first position in the slide element 26, releases the insertion head 12 from the retention means and drives it down for application of the insertion head 12 on the body of a patient, with the cannula 11 penetrating into the body ahead of it, until the cannula 11 is completely inserted and the insertion head 12 lies with its underside, which is here formed by an adhesive plaster 32, on the surface of the body. The retention element 26 with the retention means remains unmoved relative to the housing 1 in the upper position and, for application of a further insertion head 12, first has to be brought back to the engage position, by turning the rotary knob 25 relative to the housing 1 so as to overcome an initially high resistance. Since the cylindrical section of the retention element 26 has guides 33 which are shaped like spiral sections and which alternately turn left and right, it is immaterial whether the rotary knob 25 is turned right or left for transferring the insertion device from the engage position to the standby position or for resetting the retention element after the application, since any rotation, in whichever direction, in each case leads to the state that is wanted.

Although three different embodiments of the insertion device according to the present invention have been described above, it should be noted that the technical solutions shown in the illustrative embodiments can of course also be combined with one another to form further inventive embodiments of the insertion device.

Embodiments of the present invention, including preferred embodiments, have been presented for the purpose of illustration and description. They are not intended to be exhaustive or to limit the invention to the precise forms and steps disclosed. The embodiments were chosen and described to provide the best illustration of the principles of the invention and the practical application thereof, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

The invention claimed is:

1. An insertion device for an infusion set, the device comprising a retainer by which the infusion set can be temporarily held on the device and a driver comprising a pretensionable spring for providing drive energy for an insertion movement of the infusion set, wherein the infusion set is secured by the retainer by clamping when the retainer is in an engage position and can then be moved, with simultaneous pretensioning of the spring, to an insertion movement starting position, wherein the infusion set is already separated from the retainer at the start of the insertion movement, and wherein the infusion set moves through at least part of the insertion movement free of the retainer.

2. An insertion device for an insertion head with at least one infusion cannula and/or with at least one puncturing tip for introduction into the body of a patient, comprising:
    a) at least one contact face for placing the insertion device onto an application site on the body of the patient for application of the insertion head,
    b) retention means with which the insertion head that is to be applied is temporarily held on the insertion device,
    c) drive means for effecting an insertion movement of the insertion head relative to the contact face, in the longitudinal direction of the at least one infusion cannula or puncturing tip of the insertion head ready for application, from a first position, in which the insertion head ready for application is held by the retention means such that the at least one infusion cannula and puncturing tip are set back relative to the contact face, to a second position, in which the at least one infusion cannula and puncturing tip protrude beyond the contact face to permit introduction of the at least one infusion cannula and puncturing tip into the body of the patient when the insertion movement is executed with the contact face of the insertion device placed on the body, wherein the drive means has at least one pretensionable energy-storing element for providing the drive energy, and the retention means are able to be positioned relative to the contact face in an engage position and in a standby position and are able to hold the insertion head in the engage position, and wherein the retention means, starting from the engage position, can then be brought to the standby position with the insertion head held on them, and, on reaching the standby position, the retention means hold the insertion head in the first position ready for application, whereby, at the start of the insertion movement, the insertion head is separated from the retention means such that it can execute at least a greater part of the insertion movement free of the retention means, and wherein the pretensionable energy-storing element is pretensioned upon the movement of the retention means from the engage position to the standby position.

3. The insertion device according to claim 2, wherein in the standby position the insertion head is held by the retention means in the first position purely with a force fit, purely with a form fit, or with a combination of a force fit and form fit.

4. The insertion device according to claim 3, wherein in the engage position, the insertion head is held by the retention means purely with a form fit or with a combination of a force fit and form fit, and the form fit is cancelled during the movement of the retention means, with the insertion head held therein, from the engage position to the standby position.

5. The insertion device according to claim 3, wherein in the engage position, the insertion head is held by the retention means purely with a force fit, and the force fit is reduced during the movement of the retention means, with the insertion head held therein, from the engage position to the standby position.

6. The insertion device according to claim 2, wherein during one of most or all of the insertion movement the retention means remain unmoved relative to the contact face.

7. The insertion device according to claim 2, further comprising a manually activatable actuation means comprising one of a slide element, a rotary knob or a push button, by which the retention means, with the insertion head held thereon, can be brought manually from the engage position to the standby position, with pretensioning of the energy-storing element.

8. The insertion device according to claim 7, further comprising a housing, the retention means being connected to a slide element which can be gripped by hand and can be moved relative to the housing to move the retention means from the engage position to the standby position, with pretensioning of the energy-storing element.

9. The insertion device according to claim 2, wherein the overall dimensions of the device remain unchanged during the movement of the retention means from the engage position to the standby position.

10. The insertion device according to claim 2, wherein the pretensionable energy-storing element can be pretensioned repeatedly to permit repeated use of the insertion device for application of an insertion head.

11. The insertion device according to claim 2, wherein with the insertion head located in the first position, the energy-storing element can be made ready in the pretensioned state, and the insertion movement can then be triggered by actuation of at least one actuation member, with increasing relaxation of the energy-storing element.

12. The insertion device according to claim 11, wherein the drive means comprises a thrust element for transmitting the drive energy to the insertion head to be applied and, by displacing the thrust element counter to the direction of the insertion movement and subsequently locking it with a locking means that can be released by the actuation members, the energy-storing element can be pretensioned and made ready in the pretensioned state.

13. The insertion device according to claim 12, further comprising at least two actuation members, which have to be actuated simultaneously to trigger the insertion movement, a first of the actuation members being actuated by the contact face of the insertion device being pressed onto the body of the patient in the direction of the insertion movement of the insertion head.

14. The insertion device according to claim 13, wherein the first actuation member is a slide-shaped or button-shaped element which forms all the contact faces.

15. The insertion device according to claim 13, wherein a second actuation member is a button-shaped element which can be pressed in a direction transverse to the direction in which the insertion device is pressed onto the body of the patient.

16. The insertion device according to claim 15, wherein the at least two actuation members are operatively connected to one another such that, by actuating one actuation member, a blocking of the other actuation member can be cancelled.

17. The insertion device according to claim 16, wherein the actuation member or the actuation members can be actuated with one hand to permit one-handed triggering of the insertion movement.

18. The insertion device according to claim 17, wherein when an actuating force ceases the actuation members automatically go back to an unactuated state.

19. The insertion device according to claim 2, wherein the energy-storing element is one of a helical spring, leg spring or leaf spring made of metal or plastic, a rubber spring element, or a pneumatic compression spring.

20. The insertion device according to claim 2, further comprising a displacement means for effecting a transverse displacement of a displaceable actuation member associated with the insertion head to permit automatic deployment of all the deployable infusion cannulas and puncturing tips of the insertion head during the movement of the retention means from the engage position to the standby position.

21. The insertion device according to claim 20, wherein the displacement means for effecting a displacement of a displaceable actuation member comprises a ramp surface on which the transversely displaceable actuation member can run during the movement of the retention means, with the insertion head held therein, from the engage position to the standby position and in so doing can be displaced transverse to the direction of movement of the retention means and of the insertion head.

22. The insertion device according to claim 21, wherein the displacement means for effecting a displacement of a displaceable actuation member comprises a lever mechanism.

23. An arrangement comprising an insertion device and an insertion head, the insertion device comprising a retainer by which the insertion head can be temporarily held on the device and driver comprising a pretensionable spring for providing drive energy for an insertion movement of the insertion head, wherein the insertion head is secured by the retainer by clamping when the retainer is in an engage position and can then be moved, with simultaneous pretensioning of the spring, to an insertion movement starting position, wherein the insertion head is already separated from the retainer at the start of the insertion movement, and wherein the insertion head moves through at least part of the insertion movement free of the retainer, the insertion head comprising at least one infusion cannula and/or at least one puncturing tip.

24. The arrangement according to claim 23, wherein the at least one infusion cannula and/or puncturing tip are deployable and folded inwardly in the unactuated state, in which the insertion head is intended to be received in the retainer arranged in the engage position or is already received in the retainer arranged in the engage position, and wherein the at least one deployable infusion cannula and/or puncturing tip are deployed during the movement of the retainer, with the insertion head held correctly therein, from the engage position to the standby position.

25. The arrangement according to claim 24, wherein the insertion head comprises at least one of an infusion set, port and sensor arrangement.

26. A method for applying an insertion head to the body of a patient, in particular an insertion head designed as an infusion set, port and/or sensor arrangement and having at least one infusion cannula and/or at least one puncturing tip, using an insertion device comprising:
 a) at least one contact face for placing the insertion device onto an application site on the body of the patient for application of the insertion head;
 b) retention means with which the insertion head that is to be applied is temporarily held on the insertion device;
 c) drive means for effecting an insertion movement of the insertion head relative to the contact face, in the longitudinal direction of an infusion cannula or puncturing tip of the insertion head ready for application, from a first position, in which the insertion head ready for application is held by the retention means such that all the infusion cannulas and puncturing tips of the insertion head are set back relative to the contact face, to a second position, in which all the infusion cannulas and puncturing tips of the insertion head protrude substantially completely beyond the contact face, in order to permit introduction of all the infusion cannulas and puncturing tips of the insertion head into the body of the patient when the insertion movement is executed with the contact face of the insertion device placed on the body, wherein the drive means has at least one pretensionable energy-storing element for providing the drive energy, and the retention means is able to be positioned relative to the contact face in an engage position and in a standby position and is designed such that the insertion head to be applied can be arranged on the retention means in the engage position such that it is held, and the retention means, starting from the engage position, can then be brought to the standby position with the insertion head held, and, on reaching the standby position, the retention means holds the insertion head in the first position ready for application, and wherein, at the start of the insertion movement, the insertion head is separated from the retention means, such that it can execute at least the greatest part of the insertion movement free of the retention means, and the pretensionable energy-storing element is pretensioned upon the movement of the retention means from the engage position to the standby position, said method comprising the steps of:

a) making ready the insertion device, with the retention means arranged in the engage position;

b) engaging the insertion head with the retention means such that the insertion head is held thereby;

c) moving the retention means from the engage position, with the insertion head held thereon, and with pretensioning of the pretensionable energy-storing element, to the standby position in which the insertion head is held ready for application in the first position by the retention means;

d) arranging the insertion device with the contact face on the desired application site on the body of the patient such that all the infusion cannulas and puncturing tips of the insertion head can penetrate correctly into the body during the insertion movement; and e) triggering the insertion movement, whereby the insertion head is separated from the retention means at the start of the insertion movement, such that it executes at least the greatest part of the insertion movement free of the retention means.

27. The method according to claim 26, wherein the insertion head is held in the first position by the retention means purely with a force fit, purely with a form fit, or with a combination of a force fit and form fit.

28. The method according to claim 27, wherein the insertion head in the engage position is held by the retention means purely with a form fit or with a combination of a force fit and form fit and, in particular, the form fit is cancelled during the movement of the retention means from the engage position to the standby position.

29. The method according to claim 27, wherein the insertion head in the engage position is held by the retention means purely with a force fit and, in particular, the force fit is reduced during the movement of the retention means from the engage position to the standby position.

30. The method according to claim 29, wherein the retention means is held unmoved relative to the contact face, at least during a large part of the insertion movement or during the entire insertion movement of the insertion head.

31. The method according to claim 30, wherein the retention means, with the insertion head held thereon, can be brought manually by muscle force from the engage position to the standby position by one of displacing a slide element, turning a rotary knob or pressing a push button.

32. The method according to claim 31, wherein the energy-storing element is made ready in the pretensioned state, and the insertion movement is then triggered by actuating an actuation member.

33. The method according to claim 32, wherein arranging the insertion device on the body of the patient and triggering the insertion movement is done with one hand.

34. The method according to claim 33, wherein an insertion head with at least one deployable infusion cannula and/or at least one deployable puncturing tip, and in a state in which all the deployable infusion cannulas and puncturing tips of the insertion head are folded inwardly, is fitted into the retention means, and all the deployable infusion cannulas and puncturing tips of the insertion head are deployed during the movement of the retention means, with the insertion head held therein, from the engage position to the standby position.

* * * * *